United States Patent [19]
Meinhardt et al.

[11] Patent Number: 5,969,035
[45] Date of Patent: Oct. 19, 1999

[54] THICKENING OF LOW MOLECULAR WEIGHT SILOXANES WITH ACRYLATE/METHACRYLATE POLYETHER GRAFTED SILICONE ELASTOMERS

[76] Inventors: David Randall Meinhardt, 5009 Plainfield, Midland, Mich. 48642; Shizhong Zhang, 315 E. Chapel La., Midland, Mich. 48640

[21] Appl. No.: 09/019,578

[22] Filed: Feb. 6, 1998

[51] Int. Cl.$^6$ ................................................. C08G 77/08
[52] U.S. Cl. ........................... 524/731; 524/862; 524/588; 524/268; 528/15; 528/26; 528/25; 424/401; 525/479
[58] Field of Search ................................. 528/15, 26, 25; 524/731, 862, 588, 268; 424/401; 525/479

[56] References Cited

U.S. PATENT DOCUMENTS

| | | | |
|---|---|---|---|
| 4,311,695 | 1/1982 | Starch | 424/184 |
| 4,987,169 | 1/1991 | Kuwata | 524/267 |
| 5,236,986 | 8/1993 | Sakuta | 524/267 |
| 5,412,004 | 5/1995 | Tachibana | 524/27 |
| 5,654,362 | 8/1997 | Schulz | 524/862 |
| 5,811,487 | 9/1998 | Schulz, Jr. et al. | 524/862 |

*Primary Examiner*—Margaret G. Moore

[57] ABSTRACT

Low molecular weight siloxane fluids are thickened by silicone elastomers. The silicone elastomers are made by crosslinking reactions of ≡Si—H containing siloxanes and an unsaturated hydrocarbon such as an alpha, omega-diene, in the presence of a low molecular weight siloxane fluid. The ≡SiH siloxane is first partially reacted with either a monoacrylate functionalized polyether or a monomethacrylate functionalized polyether. It is then crosslinked by the alpha, omega-diene in the presence of the low molecular weight siloxane fluid. An elastomer, i.e. gel, with polyether groups is produced. The elastomer gel can be swollen with the low molecular weight siloxane fluid under shear force to provide a uniform silicone paste. The silicone paste has excellent spreadability upon rubbing, and possesses unique Theological properties in being thixotropic and shear thinning. The silicone paste can be easily emulsified with water to form a stable uniform emulsion without using a surfactant to allow normally immiscible materials to become intimately mixed.

18 Claims, No Drawings

THICKENING OF LOW MOLECULAR WEIGHT SILOXANES WITH ACRYLATE/ METHACRYLATE POLYETHER GRAFTED SILICONE ELASTOMERS

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to the thickening of low molecular weight siloxane fluids or solvents. More particularly, the siloxane fluids or solvents are swollen by a silicone elastomer, i.e., a silicone gel.

The swollen silicone elastomer gel can be used in that form, or it can be converted into a silicone paste or a silicone emulsion, if desired.

BACKGROUND OF THE INVENTION

Cross-links are junctions of polymer strands in a three-dimensional network. They may be viewed as long-chain branches which are so numerous that a continuous insoluble network or gel is formed.

Platinum catalyzed hydrosilylation reactions have been used to form networks. Typically, such reactions involve a low molecular weight siloxane containing $\equiv$Si—H groups, and a high molecular weight siloxane containing $\equiv$Si-vinyl groups, or vice versa.

Attractive features of this mechanism are that (i) no by-products are formed, (ii) cross-linking sites and hence network architecture can be narrowly defined, and (iii) hydrosilylation will proceed even at room temperature to form the networks. In the mechanism, crosslinking involves addition of $\equiv$SiH across double bonds, i.e., $\equiv$SiH+ $CH_2$=CH—R→$\equiv$SiCH$_2$CH$_2$—R; or crosslinking involves addition of $\equiv$SiH across triple bonds, i.e., $\equiv$SiH+HC$\equiv$C—R→$\equiv$SiCH=CH—R.

We have utilized this mechanism, but by employing some unobvious and unique modifications of the mechanism, we have been able to formulate a new range of product forms having new and unique properties and ranges of application.

In particular, one unique aspect is that our silicone paste can be used to form an emulsion without the need of a surfactant. This can be of considerable value in the personal care arena where skin sensitivity due to the presence of certain surfactants can be an issue.

BRIEF SUMMARY OF THE INVENTION

Our invention relates to a method of making a silicone elastomer by a first step of reacting (A) an $\equiv$Si—H containing polysiloxane; and (B) either a monoacrylate functionalized polyether or a monomethacrylate functionalized polyether; in the presence of a platinum catalyst, until an $\equiv$Si—H containing siloxane with polyether groups is formed, i.e., a polysiloxane containing polyether substituents and residual silicon hydride groups. In a second step according to our method, we react (C) the polysiloxane containing polyether substituents and residual silicon hydride groups; and (D) an unsaturated hydrocarbon such as an alpha, omega-diene; in the presence of (E) a solvent and a platinum catalyst, until a silicone elastomer is formed by crosslinking and addition of $\equiv$SiH across double bonds in the alpha, omega-diene.

As another feature of our invention, additional solvent can be added to the silicone elastomer while the solvent and silicone elastomer are sheared until a silicone paste is formed.

As a further feature of our invention, water is added to the silicone paste, and the water and silicone paste are sheared until a silicone emulsion is formed. The silicone emulsion is formed free of the presence of a surfactant.

Silicone elastomers, silicone pastes, and silicone emulsions, prepared according to these methods, have particular value and utility in treating hair, skin, or underarm areas of the human body. In addition, the silicone elastomers, silicone pastes, and silicone emulsions, are capable of forming barrier films after evaporation of any solvent or volatile component.

These and other features and objects of our invention will become apparent from a consideration of the detailed description.

BRIEF DESCRIPTION OF THE SEVERAL VIEWS OF THE DRAWING

Not applicable.

DETAILED DESCRIPTION OF THE INVENTION

Our invention, and the various steps carried out according to our process, can be illustrated with reference to the procedure as shown below.

Step 1: Incorporation of the polyether
$\equiv$SiH siloxane+acrylate polyether+platinum catalyst→siloxane with polyether groups and residual $\equiv$SiH Step 2: Gelation
siloxane with polyether groups and residual $\equiv$SiH+ $\equiv$SiH siloxane (optional)+alpha, omega-diene+low molecular weight siloxane fluid+platinum catalyst→gel (elastomer)

Step 3: Shearing and swelling
gel (elastomer)+siloxane fluid+shear→paste

Step 4: Emulsification
silicone paste+water+shear→silicone emulsion

In Step 1, the molar ratio of the polyether to the $\equiv$SiH in the siloxane should be in the range of 0.01 to less than 1.0.

In Step 2, the weight ratio of the low molecular weight siloxane fluid to the weight of the $\equiv$SiH siloxane with polyether groups and the alpha, omega-diene can be from 1–98, but preferably is between 3–10. The molar ratio of the $\equiv$SiH groups in the siloxane with polyether groups to unsaturated groups in the alpha, omega-diene can be from 20:1 to 1:20, but preferably is 1:1. While Step 2 can include a mixture of various types of compounds, at least one $\equiv$SiH containing siloxane must include a polyether group.

For example, one formulation found especially suitable for Step 2 is a mixture containing the following compounds:

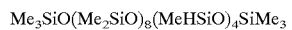

1,5-hexadiene, and decamethylcyclopentasiloxane.

In the above formulas, Me represents the group —CH$_3$ and Q represents the group —CH$_2$CH(CH$_3$)C(O) (OCH$_2$CH$_2$)$_9$OCH$_3$.

In Step 3, the silicone paste should contain 80–98 percent by weight of the low molecular weight siloxane fluid or other fluid or solvent to be thickened.

In Step 4, the weight ratio of water to the silicone paste can be from 95:5 to 5:95.

The $\equiv$Si—H containing polysiloxane is represented by compounds of the formula $R_3SiO(R'_2SiO)_a(R''HSiO)_bSiR_3$ referred to as type $A^1$, and compounds of the formula $HR_2SiO(R'_2SiO)_cSiR_2H$ or compounds of the formula $HR_2SiO(R'_2SiO)_a(R''HSiO)_bSiR_2H$ referred to as type $A^2$. In the three formulas, R, R', and R", are alkyl groups with 1–6 carbon atoms; a is 0–250; b is 1–250; and c is 0–250. The molar ratio of compounds $A^2:A^1$ is 0–20, preferably 0–5. In preferred embodiments, compounds of types $A^1$ and $A^2$ are used in the reaction, however, it is possible to successfully conduct the reaction using only compounds of type $A^1$. If desired, these $\equiv$Si—H containing polysiloxanes can also include trifunctional T units $RSiO_{3/2}$ and tetrafunctional Q units $SiO_{4/2}$.

The $\equiv$Si—H containing polysiloxane $A^1$ can also comprise an alkylhydrogen cyclosiloxane or an alkylhydrogendialkyl cyclosiloxane copolymer, represented in general by the formula $(R'_2SiO)_d(R''HSiO)_e$ where R' and R" are as defined above, d is 0–10, and e is 3–10. Some representative compounds are $(OSiMeH)_4$, $(OSiMeH)_3(OSiMeC_6H_{13})$, $(OSiMeH)_2(OSiMeC_6H_{13})_2$, and $(OSiMeH)(OSiMeC_6H_{13})_3$, where Me represents —$CH_3$. If desired, these $\equiv$Si—H containing polysiloxanes can also include trifunctional T units $RSiO_{3/2}$ and tetrafunctional Q units $SiO_{4/2}$.

The most preferred unsaturated hydrocarbon is an alpha, omega-diene of the formula $CH_2$=$CH(CH_2)_xCH$=$CH_2$ where x is 1–20. Some representative examples of suitable alpha, omega-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

However, other unsaturated hydrocarbons can be used such as alpha, omega-diynes of the formula $CH\equiv C(CH_2)_xC\equiv CH$; or alpha, omega-ene-ynes of the formula $CH_2$=$CH(CH_2)_xC\equiv CH$ where x is 1–20. Some representative examples of suitable alpha, omega-diynes for use herein are 1,3-butadiyne $HC\equiv C$—$C\equiv CH$ and 1,5-hexadiyne (dipropargyl) $HC\equiv C$—$CH_2CH_2$—$C\equiv CH$. One representative example of a suitable alpha, omega-ene-yne for use herein is hexene-5-yne-1 $CH_2$=$CHCH_2CH_2C\equiv CH$.

In addition, our invention contemplates the use of other types of unsaturated materials such as siloxane monomers or siloxane polymers containing two or more terminal alkenyl groups; two or more pendant alkenyl groups; or two or more terminal and pendant groups. One suitable siloxane, for example, is 1,3-divinyltetramethyldisiloxane $H_2C$=$CH(CH_3)_2SiOSi(CH_3)_2CH$=$CH_2$. Representative of further siloxanes which can be employed are vinyl terminated polydimethylsiloxanes containing more than two silicon atoms; vinyl terminated diphenylsiloxane-dimethylsiloxane copolymers; vinyl terminated polyphenylmethylsiloxanes; vinyl terminated trifluoropropylmethylsiloxane-dimethylsiloxane copolymers; vinyl terminated diethylsiloxane-dimethylsiloxane copolymers; trimethylsiloxy terminated vinylmethylsiloxane-dimethylsiloxane copolymers; vinyl terminated vinylmethylsiloxane-dimethylsiloxane copolymers; and vinylmethylsiloxane homopolymers.

The reactions in Steps 1 and 2 requires a catalyst to effect the reaction between the $\equiv$SiH containing siloxanes, the monoacrylate/monomethacrylate functionalized polyether, and the alpha, omega-diene. Suitable catalysts are Group VIII transition metals, i.e., the noble metals. Such noble metal catalysts are described in U.S. Pat. No. 3,923,705, incorporated herein by reference, to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex, typically containing about one weight percent of platinum or less, carried in a polydimethylsiloxane fluid or in a solvent such as toluene.

The particular catalyst used in our examples was Karstedt's catalyst as a 0.5 weight percent of platinum carried in a two centistoke ($mm^2/s$) polydimethylsiloxane fluid. Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are used in amounts from 0.00001–0.5 parts per 100 weight parts of $\equiv$SiH containing polysiloxane, preferably 0.00001–0.02 parts, most preferably 0.00001–0.002 parts.

The monoacrylate functionalized polyether used herein is a compound of the formula $CH_2$=$CHCOO[CH_2CH_2O]_m[CH_2CH(CH_3)O]_n[CH_2CH(CH_2CH_3)O]_pT$. The monomethacrylate functionalized polyether used herein is a compound of the formula $CH_2$=$C(CH_3)COO[CH_2CH_2O]_m[CH_2CH(CH_3)O]_n[CH_2CH(CH_2CH_3)O]_pT$. In these formulas, T represents an end group which can be hydrogen; a C1–C30 linear or branched chain alkyl group such as methyl, ethyl, propyl, butyl, decyl, and octadecyl; an aryl group such as phenyl; or a C1–C20 acyl group such as acetyl, propionyl, butyryl, lauroyl, myristoyl, and stearoyl. m, n, and p, each represent integers which can be equal to zero or have values of 1–100. Most preferably, however, m, n, and p, should not all be equal to zero. Such monoacrylate functionalized polyethers and monomethacrylate functionalized polyethers are commercially available from companies such as the Sartomer Company of West Chester, Pa. under the trademark SARTOMER®.

In a case where m, n, and p, are all equal to zero, and T is a long alkyl group such as C18, for example, the resulting silicone elastomeric product would be rendered more hydrophobic, with the result that the silicone paste would be more compatible with aliphatic materials such as hydrocarbon waxes and mineral oil.

The phrase low molecular weight siloxane fluid is intended to include (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS).

VMS compounds correspond to the average unit formula $(CH_3)_aSiO_{(4-a)/2}$ in which a has an average value of two to three. The compounds contain siloxane units joined by $\equiv$Si—O—Si$\equiv$ bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH_3)_3SiO\{(CH_3)_2SiO\}_ySi(CH_3)_3$. The value of y is 0–5. Cyclic VMS have the formula $\{(CH_3)_2SiO\}_z$. The value of z is 3–6. Preferably, these volatile methyl siloxane have a boiling point less than about 250° C. and a viscosity of about 0.65–5.0 centistoke (mm²/s).

Representative linear volatile methyl siloxanes are hexamethyldisiloxane (MM) with a boiling point of 100° C., viscosity of 0.65 mm²/s, and formula Me₃SiOSiMe₃; octamethyltrisiloxane (MDM) with a boiling point of 152° C., viscosity of 1.04 mm²/s, and formula Me₃SiOMe₂SiOSiMe₃; decamethyltetrasiloxane (MD₂M) with a boiling point of 194° C., viscosity of 1.53 mm²/s, and formula Me₃SiO(Me₂SiO)₂SiMe₃; dodecamethylpentasiloxane (MD₃M) with a boiling point of 229° C., viscosity of 2.06 mm²/s, and formula Me₃SiO(Me₂SiO)₃SiMe₃; tetradecamethylhexasiloxane (MD₄M) with a boiling point of 245° C., viscosity of 2.63 mm²/s, and formula Me₃SiO (Me₂SiO)₄SiMe₃; and hexadecamethylheptasiloxane (MD₅M) with a boiling point of 270° C., viscosity of 3.24 mm²/s, and formula Me₃SiO(Me₂SiO)₅SiMe₃.

Representative cyclic volatile methyl siloxanes are hexamethylcyclotrisiloxane (D₃) a solid with a boiling point of 134° C. and formula {(Me₂)SiO}₃; octamethylcyclotetrasiloxane (D₄) with a boiling point of 176° C., viscosity of 2.3 mm²/s, and formula {(Me₂)SiO}₄; decamethylcyclopentasiloxane (D₅) with a boiling point of 210° C., viscosity of 3.87 mm²/s, and formula {(Me₂)SiO}₅; and dodecamethylcyclohexasiloxane (D₆) with a boiling point of 245° C., viscosity of 6.62 mm²/s, and formula {(Me₂)SiO}₆.

Representative branched volatile methyl siloxanes and are heptamethyl-3-{(trimethylsilyl)oxy}trisiloxane (M₃T) with a boiling point of 192° C., viscosity of 1.57 mm²/s, and formula C₁₀H₃₀O₃Si₄; hexamethyl-3,3,bis {(trimethylsilyl)oxy} trisiloxane (M₄Q) with a boiling point of 222° C., viscosity of 2.86 mm²/s, and formula C₁₂H₃₆O₄Si₅; and pentamethyl {(trimethylsilyl)oxy} cyclotrisiloxane (MD₃) with the formula C₈H₂₄O₄Si₄.

Our process can include the use of low molecular weight linear and cyclic volatile and non-volatile alkyl and aryl siloxanes. Representative linear polysiloxanes are compounds of the formula R₃SiO(R₂SiO)ySiR₃, and representative cyclic polysiloxanes are compounds of the formula (R₂SiO)z. R is an alkyl group of 1–6 carbon atoms, or an aryl group such as phenyl. The value of y is 0–80, preferably 0–20. The value of z is 0–9, preferably 4–6. These polysiloxanes have a viscosity generally in the range of about 1–100 centistoke (mm²/s).

Other representative low molecular weight non-volatile polysiloxanes have the general structure:

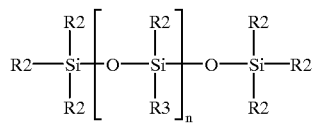

where n has a value to provide polymers with a viscosity in the range of about 100–1,000 centistoke (mm²/sec).

R2 and R3 are alkyl radicals of 1–20 carbon atoms, or an aryl group such as phenyl. Typically, the value of n is about 80–375. Illustrative polysiloxanes are polydimethylsiloxane, polydiethylsiloxane, polymethylethylsiloxane, polymethylphenylsiloxane, and polydiphenylsiloxane.

Low molecular weight functional polysiloxanes can be represented by acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

Our invention is not limited to swelling silicone elastomers with only low molecular weight polysiloxanes. Other types of solvents can swell the silicone elastomer. Thus, a single solvent or a mixture of solvents may be used.

By solvent we mean (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, Varnish Makers and Painters (VM&P) naphtha, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

We further intend to encompass by the term solvent, volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, we intend the term solvent to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Our process is carried out stepwise by combining the ≡SiH containing siloxane(s), the monoacrylate functionalized polyether or the monomethacrylate functionalized polyether, the alpha, omega-diene, the low molecular weight siloxane or solvent, and the platinum catalyst; and mixing these ingredients at room temperature until a gel, elastomer, paste, or emulsion, is formed. If desired, the gel, elastomer, paste, or emulsion, can be further diluted with an additional similar or dissimilar solvent(s), to form the final composition. A blend of hexane and tetrahydrofuran, a fragrance, an oil, or another low molecular weight siloxane, are examples of diluents that could be so employed. Higher temperatures to speed up the process can be used.

Additional amounts of low molecular weight siloxane or solvent can be added to the gel, i.e., Step 3, while the resulting mixture is subjected to shear force to form the paste. In Step 4, shear force is again used, during or after water is added to the paste to form the emulsion. Any type of mixing and shearing equipment may be used to perform these steps such as a batch mixer, planetary mixer, single or multiple screw extruder, dynamic or static mixer, colloid mill, homogenizer, sonolator, or a combination thereof.

Typically, we carry out the process using approximately a 1:1 molar ratio of the ≡Si—H containing siloxane with polyether groups and the alpha, omega-diene. It is expected that useful materials may also be prepared by carrying out the process with an excess of either the ≡Si—H containing siloxane or the alpha, omega-diene, but this would be considered a less efficient use of the materials. The remainder of the composition comprises the low molecular weight siloxane or solvent, in amounts generally within the range of about 65–98 percent by weight of the composition, but preferably about 80–98 percent by weight.

EXAMPLES

The following examples are set forth for the purpose of illustrating our invention in more detail.

Example 1

50 gram of an organopolysiloxane with the average structure $Me_3SiO(Me_2SiO)_{93}(MeHSiO)_6SiMe_3$ where Me is —$CH_3$, 2.98 gram of $CH_2=C(CH_3)COO(CH_2CH_2O)_9CH_3$ a compound sold under the trademark Sartomer® CD-550 by the Sartomer Company of West Chester, Pa., and 231.40 gram of decamethylcyclopentasiloxane ($D_5$) were mixed and heated to 100° C., and then 0.577 gram of Karstedt's catalyst containing 0.5 weight percent platinum was added. After 20 minutes, 15.606 gram of a mixture containing 10% by weight of 1,5-hexadiene $H_2C=CHCH_2CH_2CH=CH_2$ and 90% by weight of decamethylcyclopentasiloxane was added to the solution. Gelation occured within one hour. The gel was heated in an oven at 70° C. for about two hours. Then one part by weight of the gel was swollen with one part by weight of decamethylcyclopentasiloxane under shear force. The resulting uniform paste had a viscosity of 90,000 cP (mPa•s). The paste was mixed with deionized water in a 5:1 weight ratio in a glass jar using a mechanical stirrer. A smooth opaque white emulsion formed having a viscosity of 126,000 cP (mPa•s). Viscosity was measured using a Brookfield DV-II Viscometer having a TC-type spindle operating at 2.5 rpm (0.26 rad/s).

Example 2

50 gram of an organopolysiloxane having the average structure $Me_3SiO(Me_2SiO)_{93}(MeHSiO)_6SiMe_3$, 2.98 gram of $CH_2=C(CH_3)COO(CH_2CH_2O)_9CH_3$, i.e., Sartomer® CD-550, and 298.09 gram of decamethylcyclopentasiloxane were mixed and heated to 100° C., and then 0.701 gram of Karstedt's catalyst containing 0.5 weight percent of platinum was added. After 20 minutes, 13.259 gram of a silicone polymer having the average structure $(Vi)Me_2SiO(SiMe_2O)_8SiMe_2(Vi)$ where Vi is $H_2C=CH-$ was added. Gelation occured within one hour. The gel was heated in an oven at 70° C. for about two hours. Then one part by weight of the gel was swollen with one part by weight of decamethylcyclopentasiloxane under shear force. The resulting uniform paste had a viscosity of 63,000 cP (mPa•s). The paste was mixed with deionized water in a 5:1 weight ratio in a glass jar using a mechanical stirrer. A smooth opaque white emulsion was formed having a viscosity of 78,000 cP (mPa•s).

Example 3 - Comparative 50 gram of the copolymer $Me_3SiO(Me_2SiO)_{93}(MeHSiO)_6SiMe_3$ used in Examples 1 and 2, and 229.92 gram of decamethylcyclopentasiloxane were mixed and heated to 70° C. Then 0.583 gram of Karstedt's catalyst containing 0.5 weight percent of platinum, and 17.835 gram of a mixture containing 10% by weight of 1,5-hexadiene and 90% by weight of decamethylcyclopentasiloxane was added to the solution. Gelation occured within a few minutes. The gel was heated in an oven at 70° C. for about 3 hours. Then seven parts by weight of the gel was swollen with five parts by weight of decamethylcyclopentasiloxane under shear force. The resulting uniform paste had a viscosity of 100,000 cP (mPa•s). The paste was mixed with deionized water in a 5:1 weight ratio in a glass jar using a mechanical stirrer. In this example, however, water could not be dispersed.

The silicone elastomer, silicone gel, and silicone paste compositions of our invention have particular value in the personal care arena. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they will function as leveling and spreading agents for pigments in make-ups, color cosmetics, foundations, blushes, lipsticks, lip balms, eyeliners, mascaras, oil removers, color cosmetic removers, and powders. They are useful as delivery systems for oil and water soluble substances such as vitamins. When incorporated into sticks, gels, lotions, aerosols, and roll-ons, the compositions impart a dry, silky-smooth, payout.

In addition, the compositions exhibit a variety of advantageous and beneficial properties such as clarity, shelf stability, and ease of preparation. Hence, they have wide application, but especially in antiperspirants, deodorants, in perfumes as a carrier, and for conditioning hair.

Our silicone elastomers, gels, and pastes have uses beyond the personal care arena, including their use as a filler or insulation material for electrical cable, a soil or water barrier, or as a replacement for epoxy materials used in the electronics industry.

They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying rheological, physical, or energy absorbing properties of such phases in either their neat or finished condition.

In addition, our silicone elastomers, gels, and pastes are capable of functioning as carriers for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid.

Our invention, therefore, provides another viable route to the production of a stable uniform emulsion without employing a surfactant, allowing normally immiscible materials to become intimately mixed, by using a monoacrylate functionalized polyether or a monomethacrylate functionalized polyether, in lieu of a mono-alkenyl functionalized polyether according to prior copending application U.S. Ser. No. 08/768,064, filed on Dec. 16, 1996. As noted above, this can be of considerable value in the personal care arena where skin sensitivity due to the presence of certain surfactants can be an issue.

Other variations may be made in the compounds, compositions, and methods described herein without departing from the essential features of our invention. The forms of invention are exemplary only and not intended as limitations on their scope as defined in the appended claims.

We claim:

1. A method of making a silicone elastomer comprising as a first step, reacting:
   (A) an $\equiv$Si—H containing polysiloxane of the formula $R_3SiO(R'_2SiO)_a(R"HSiO)_bSiR_3$ or the formula $(R'_2SiO)_d(R"HSiO)_e$, and optionally an $\equiv$Si—H containing polysiloxane of the formula $HR_2SiO(R'_2SiO)_c SiR_2H$ or an $\equiv$Si—H containing polysiloxane of the formula $HR_2SiO(R'_2SiO)_a(R"HSiO)_bSiR_2H$, where R, R', and R" are alkyl groups with 1–6 carbon atoms, a is 0–250, b is 1–250, c is 0–250, d is 0–10, and e is 3–10; and
   (B) a monoacrylate functionalized polyether of the formula $CH_2$=$CHCOO[CH_2CH_2O]_m[CH_2CH(CH_3)O]_n[CH_2CH(CH_2CH_3)O]_pT$, or a monomethacrylate functionalized polyether of the formula $CH_2$=$C(CH_3)COO[CH_2CH_2O]_m[CH_2CH(CH_3)O]_n[CH_2CH(CH_2CH_3)O]_pT$, where T represents hydrogen; a C1–C30 linear or branched chain alkyl group, an aryl group, or a C1–C20 acyl group; and m, n, and p, each represent integers which can be equal to zero or have values of 1–100; in the presence of a platinum catalyst, until a polysiloxane is formed containing polyether substituents and residual silicon hydride groups;
   and as a second step, reacting components comprising:
   (C) the polysiloxane containing polyether substituents and residual silicon hydride groups;
   (D) an unsaturated hydrocarbon selected from the group consisting of alpha, omega-dienes of the formula $CH_2$=$CH(CH_2)_xCH$=$CH_2$, alpha, omega-diynes of the formula $CH\equiv C(CH_2)_xC\equiv CH$, and alpha, omega-ene-ynes of the formula $CH_2$=$CH(CH_2)_xC\equiv CH$, where x is 1–20, or an unsaturated siloxane monomer or siloxane polymer containing two or more terminal alkenyl groups; two or more pendant alkenyl groups; or two or more terminal and pendant groups; in the presence of
   (E) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and in the presence of a platinum catalyst, until a silicone elastomer is formed.

2. A method according to claim 1 including the further step of adding additional amounts of solvent(s) to the silicone elastomer while shearing the solvent(s) and silicone elastomer until a silicone paste is formed.

3. A method according to claim 2 including the further steps of adding water to the silicone paste, and shearing the water and silicone paste until a silicone emulsion is formed.

4. A method according to claim 3 in which the silicone emulsion is formed free of the presence of a surfactant.

5. A method according to claim 1 in which the second step includes as an additional reactant (F) an $\equiv$Si—H containing polysiloxane of the formula $R_3SiO(R'_2SiO)_a(R"HSiO)_bSiR_3$ or the formula $(R'_2SiO)_d(R"HSiO)_e$, and optionally an $\equiv$Si—H containing polysiloxane of the formula $HR_2SiO(R'_2SiO)_cSiR_2H$ or an $\equiv$Si—H containing polysiloxane of the formula $HR_2SiO(R'_2SiO)_a(R"HSiO)_bSiR_2H$, where R, R', and R" are alkyl groups with 1–6 carbon atoms, a is 0–250, b is 1–250, c is 0–250, d is 0–10, and e is 3–10.

6. A method according to claim 1 in which the solvent is a linear volatile methyl siloxane of the formula $(CH_3)_3SiO\{(CH_3)_2SiO\}_ySi(CH_3)_3$ where y is 0–5, or a cyclic volatile methyl siloxane of the formula $\{(CH_3)_2SiO\}_z$ where z is 3–8, and the volatile methyl siloxane has a boiling point less than about 250° C. and a viscosity of 0.65–5.0 centistokes $(mm^2/s)$.

7. A silicone elastomer prepared according to the method defined in claim 1.

8. A silicone paste prepared according to the method defined in claim 2.

9. A silicone emulsion prepared according to the method defined in claim 3.

10. A method of treating hair, skin, or underarm comprising applying to the hair, skin, or underarm the silicone elastomer of claim 7.

11. A method of treating hair, skin, or underarm comprising applying to the hair, skin, or underarm the silicone paste of claim 8.

12. A method of treating hair, skin, or underarm comprising applying to the hair, skin, or underarm the silicone emulsion of claim 9.

13. A method according to claim 1 in which the molar ratio of the monoacrylate functionalized polyether and the monomethacrylate functionalized polyether to the silicon hydride groups in the $\equiv$SiH containing polysiloxane is in the range of 0.01 to less than 1.0; m, n, and p, are not all equal to zero; and the $\equiv$Si—H containing polysiloxane optionally includes trifunctional T units $RSiO_{3/2}$ and tetrafunctional Q units $SiO_{4/2}$.

14. A method according to claim 13 in which in the second step, the weight ratio of the solvent to the weight of the polysiloxane containing polyether substituents and residual silicon hydride groups and the unsaturated hydrocarbon is 1–98.

15. A method according to claim 14 in which in the second step, the molar ratio of the polysiloxane containing polyether substituents and residual silicon hydride groups and the unsaturated hydrocarbon is 20:1 to 1:20.

16. A product containing the elastomer of claim 7 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, cosmetic removers, delivery systems for oil and water soluble substances, and pressed powders.

17. A product containing the paste of claim 8 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, cosmetic removers, delivery systems for oil and water soluble substances, and pressed powders.

18. A product containing the emulsion of claim 9 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, cosmetic removers, delivery systems for oil and water soluble substances, and pressed powders.

* * * * *

UNITED STATES PATENT AND TRADEMARK OFFICE
CERTIFICATE OF CORRECTION

PATENT NO. : 5,969,035
DATED : October 19, 1999
INVENTOR(S) : David Randall Meinhardt and Shizhong Zhang It is certified that error appears in the above-identified patent and that said Letters Patent is hereby corrected as shown below:

On the first page of the patent should read as follows:

Assignee: Dow Corning Corporation, Midland, Michigan

Signed and Sealed this

Twenty-first Day of November, 2000

Attest:

Q. TODD DICKINSON

*Attesting Officer*  *Director of Patents and Trademarks*